US010429279B2

(12) United States Patent
Ritterbush et al.

(10) Patent No.: US 10,429,279 B2
(45) Date of Patent: Oct. 1, 2019

(54) DEVICES AND CARTRIDGES FOR EXTRACTING BIO-SAMPLE REGIONS AND MOLECULES OF INTEREST

(71) Applicant: XMD, LLC, Sterling, VA (US)

(72) Inventors: Stephen Ritterbush, Annapolis, MD (US); Ting Pau Oei, Califon, NJ (US)

(73) Assignee: XMD, LLC, Sterling, VA (US)

( * ) Notice: Subject to any disclaimer, the term of this patent is extended or adjusted under 35 U.S.C. 154(b) by 917 days.

(21) Appl. No.: 14/341,523

(22) Filed: Jul. 25, 2014

(65) Prior Publication Data
US 2015/0104826 A1  Apr. 16, 2015

Related U.S. Application Data

(60) Provisional application No. 61/859,271, filed on Jul. 28, 2013, provisional application No. 61/874,161, filed on Sep. 5, 2013.

(51) Int. Cl.
*G01N 1/31* (2006.01)
*G01N 1/36* (2006.01)
*G01N 1/28* (2006.01)
*G01N 35/00* (2006.01)
G01N 35/02 (2006.01)

(52) U.S. Cl.
CPC ..... *G01N 1/2813* (2013.01); *G01N 35/00029* (2013.01); *G01N 1/312* (2013.01); *G01N 35/025* (2013.01); *G01N 2001/2833* (2013.01); *G01N 2035/00138* (2013.01); *Y10T 436/25375* (2015.01)

(58) Field of Classification Search
USPC ........................ 422/527, 554, 408, 68.1, 561
See application file for complete search history.

(56) References Cited

U.S. PATENT DOCUMENTS

| 6,296,809 | B1 | 10/2001 | Richards et al. |
| 6,720,191 | B1 | 4/2004 | Goldstein et al. |
| 7,695,752 | B2 | 4/2010 | Bonner et al. |
| 7,709,047 | B2 | 5/2010 | Emmert-Buck et al. |
| 8,597,715 | B2 | 12/2013 | Emmert-Buck et al. |
| 2002/0001837 | A1 | 1/2002 | Baer et al. |
| 2002/0132222 | A1 | 9/2002 | Lossing et al. |
| 2002/0182115 | A1* | 12/2002 | Aghassi ................. G01N 1/312 422/400 |
| 2001/0190177 | | 7/2010 | Emmert-Buck et al. |
| 2010/0190177 | A1 | 7/2010 | Emmert-Buck et al. |

OTHER PUBLICATIONS

International Search Report and Written Opinion issued in PCT/US2015/024837 dated Jun. 25, 2015.

* cited by examiner

*Primary Examiner* — Dean Kwak
(74) *Attorney, Agent, or Firm* — Katten Muchin Rosenman LLP

(57) ABSTRACT

Methods, devices, and systems for integrating extraction and purification of bio-sample regions and materials with patient analysis, diagnosis, follow up, and treatment. The invention provides a means to insert disclosed substrates, cartridges, and cartridge-processing instrument or instruments into a standard clinic or pathology laboratory workflow. Specifically, we disclose methods, devices, and systems for inserting standard pathology slides into disclosed cartridges and cartridge-processing instruments, either manually, semi-automatically, automatically, or by robotic means.

12 Claims, 6 Drawing Sheets

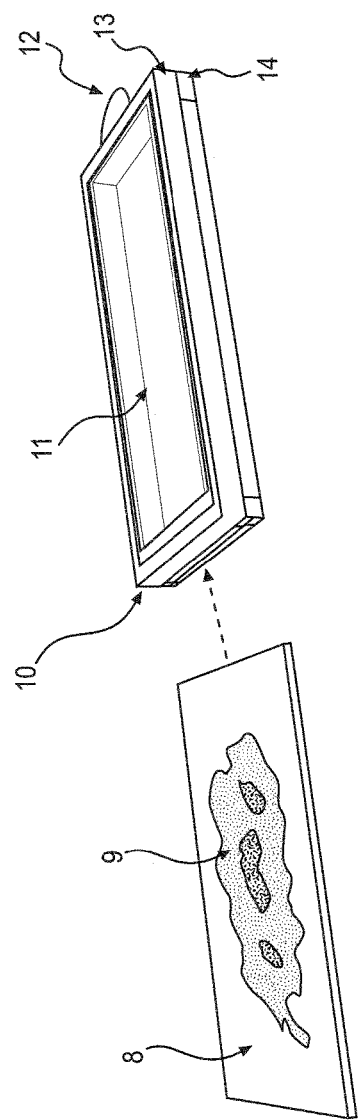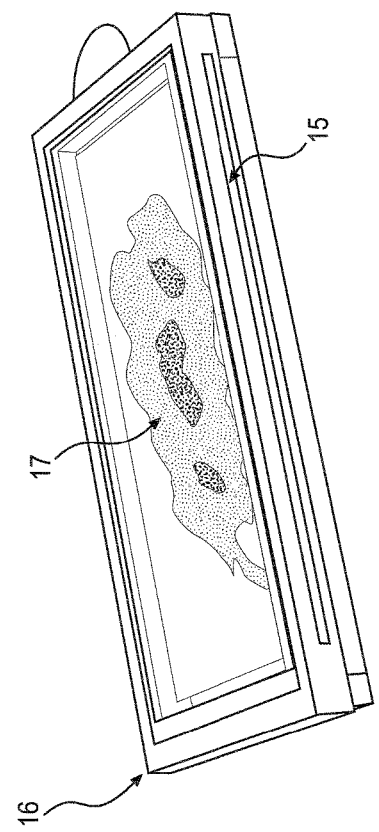
FIG. 2A
FIG. 2B

DEVICES AND CARTRIDGES FOR EXTRACTING BIO-SAMPLE REGIONS AND MOLECULES OF INTEREST

CROSS REFERENCE TO RELATED APPLICATION

This application claims the benefit of U.S. Provisional Application No. 61/859,271, filed Jul. 28, 2013; and also claims the benefit of U.S. Provisional Application No. 61/874,161, filed Sep. 5, 2013. Each of these applications is incorporated in their entirety.

FIELD OF INVENTION

The present disclosure is related to methods of extracting regions and molecules of interest from biological samples, particularly through use of an automated process utilizing specifically designed bio-cartridges.

BACKGROUND OF THE INVENTION

A variety of techniques have been used to extract specific biological targets from a biological samples obtained from patients or subjects of medical and scientific research. Traditionally, such techniques have required often difficult (and crude) manual dissection of tissue using needles or other micro-manipulation devices to obtain quantities of individual cells identified according to their visible, histological characteristics.

A key emerging challenge in effectively diagnosing patients and treating them is applying protein, nucleotide, drug and other screens to sufficient amounts of purified biological material from patient samples. For example, in order to genetically screen a cancer patient for type of cancer or for effective anti-cancer drugs or therapy, the practitioner must have enough cancer cells so that he or she can run a genetic or drug screen against those cells without being confounded by material from surrounding non-cancerous cells. In a patient sample, only a small fraction of tissue and cells may be cancerous, and those cells may occupy a complex shape in the tissue or biological sample. In order to collect enough genetic material from cancer cells, instead of from surrounding non-cancerous cells, and in order to have a good signal-to-noise ratio (more genetic material from cancerous cells than genetic material from non-cancerous cells), it is advantageous to purify disease materials from patient samples, and that purification must be integrated with subsequent patient analysis, diagnosis, follow up, and treatment.

U.S. Pat. No. 8,597,715 discloses a method of removing a target from a biological sample which involves placing a transfer surface in contact with the biological sample, and then focally altering the transfer surface to allow selective separation of the target from the biological sample. The target is a cell or cellular component of a tissue section and the transfer surface is a film that can be focally altered to adhere the target to the transfer surface. Subsequent separation of the film from the tissue section selectively removes the adhered target from the tissue section. The transfer surface is focally altered by the target (e.g. by antibody binding), and that alteration is then activated to adhere the target to the transfer surface. Such in situ alteration can be achieved by exposing the biological sample to an immunoreagent that specifically binds to the target (or a component of the target). The immunoreagent can alter the transfer surface directly (for example with a heat generating enzyme carried by the immunoreagent), or indirectly (for example by changing a characteristic of the target). Activation can occur for example by illuminating or heating the target to, adhere it to a thermoplastic transfer surface. The immunoreagent can deposit a precipitate in the target that increases its light absorption relative to surrounding tissue, such that the biological specimen can be exposed to light to selectively heat the target. Alternatively, the immunoreagent is an immunofluorescent agent that carries a fluorophore that absorbs light and emits heat. The methods and substrates disclosed in U.S. Pat. No. 8,597,715, and its related patents, U.S. Pat. Nos. 7,695,752, and 7,709,047, are incorporated herein.

Below we disclose methods, devices, and systems for integrating extraction and purification of bio-sample regions and materials with patient analysis, diagnosis, follow up, and treatment.

SUMMARY OF THE INVENTION

We disclose devices, systems, software, algorithms and methods for extracting regions and molecules of interest from biological samples. We also disclose related methods, devices, and systems for using extracted regions and molecules for better analyzing patient health, patient disease and pathology, patient follow up, and selecting most effective treatment options for patients (e.g. drugs or treatments that are found to best or better treat patients based on extracted regions and molecules from patient samples). Related analysis can include but is not limited to nucleotide screens (for the presence or absence of genetic regions), protein screens, antibody binding, drug or therapy binding (e.g. for selecting which drugs may be effective for cancer cells or other diseased cells/materials/molecules extracted from patient biological samples). We further disclose devices, systems, software, and workflows (e.g. pathology and reference lab workflows) for integrating sample extraction and the sample purification it enables (e.g. extracting cancer cells from a patient sample that contains many other types of cells) with existing and future devices, systems, and methods for patient diagnosis and treatment. For example, we disclose extraction of disease cells (e.g. cancer cells) from patient samples and integrating that extraction and purification with devices, systems, and methods found in a pathology laboratory setting, to enable improved patient diagnosis, follow up, and treatment.

In one embodiment, we disclose cartridge devices that combine a biological sample with optical, electro-magnetic or heat activated substrate or molecules that allow desired target regions of the biological sample to be extracted. A patient tissue sample, for example a tissue sample on a slide, can be inserted into or laid on top of the cartridge. Once the slide with tissue sample is inserted, the cartridge lays a substrate (e.g. a film) onto the tissue. The film can be laid onto the tissue as the slide is inserted, by for example mechanically, electrically, or optically triggering a mechanism within the cartridge that presses the film up against the tissue. Pressing can be accomplished by mechanical, hydraulic, or electrical means or by the imposition of a vacuum. Alternatively, after the slide is inserted, a user can press on the cartridge or can activate a button or switch, or the cartridge may be self-activated, to initiate contact between the substrate and the tissue.

Depending on chosen cartridge design, the tissue or biological sample may be inside the cartridge (closed cartridge) or may be still accessible from outside the cartridge (open cartridge). For example, in an open cartridge the cartridge may be only on one side of the slide with tissue, or may be designed to contact the slide with tissue at all or only some edges (for example a C shape that fits around 3 edges of a slide). The substrate that will bind to the tissue regions or molecules could be contained inside the cartridge (e.g. for closed or open cartridge) or could be applied externally (for open cartridge).

We also disclose a cartridge-assembly system and methods to make such cartridge devices for a variety of commonly encountered biological samples. In some embodiments, the cartridge and cartridge device of the present application are used for expression micro-dissection, a technique that allows for the procurement of desired cells or tissues via molecular targeting.

In some embodiments, the cartridge device comprises a biological sample sandwiched between a backing that is more rigid than the sample and a sealing film that is less rigid than the sample. The sealing film contains or has attached to it the optically or heat activated adherent.

The invention provides a means to insert disclosed substrates, cartridges, and cartridge-processing instrument or instruments into a standard clinic or pathology laboratory workflow. Specifically, we disclose methods, devices, and systems for inserting standard pathology slides into disclosed cartridges and cartridge-processing instruments, either manually, semi-automatically, automatically, or by robotic means. We further disclose methods, devices, and systems for providing substrates with their attached materials (extracted and purified tissue, cells, molecules, proteins, nucleotides) to systems and instruments to carry out genetic screening, protein screening, drug or therapy screening, as well as to systems and methods that will suggest patient diagnosis (e.g. by genetic screening, or by automated computer-vision or imaging and software processing to assess morphology and diagnose disease), will suggest and track patient follow up, and will suggest or select patient treatment. The subsequent screening and diagnosis steps could be carried out by instruments linked to our disclosed slide and cartridge-processing instruments, for example by having the slide and cartridge-processing instrument provide purified materials to a downstream DNA analysis instrument. Or, the two systems could be combined into one instrument that achieves both or more tasks.

In another embodiment, we disclose a method of analysis of extracted biological material from a subject, the method comprising: taking one or more biological samples from a subject; transferring a biological sample to one or more slides or one or more cartridges, wherein a biological sample has been mounted on the one or more slides, or wherein the one or more cartridges have been attached to one or more slides upon which a biological sample has been mounted so that a cartridge and a slide form a single unit;
inserting said one or more slides or one or more cartridges into an instrument for processing said one or more slides or one or more cartridges; extracting biological material from the biological samples on the one or more slides or one or more cartridges;
depositing extracted biological materials from one or more biological samples into individual receptacles; inserting the individual receptacles into a device for purifying biological material, including tissue, cells, nucleotides, or proteins, and wherein the instrument and the device for purifying biological material are integrated as a single unit or exist as separate units which are interfaced; transferring purified and extracted biological material to an analytical device, wherein the analytical device may conduct analyses comprising genetic or protein analysis.

In another embodiment, we disclose an automated system for analysis of extracted biological material from a subject, the device comprising: an instrument for taking one or more biological samples from a subject by automated means; a mechanism within the instrument for transfer of a biological sample to one or more slides or one or more cartridges, wherein a biological sample has been mounted on the one or more slides, or wherein the one or more cartridges have been attached to one or more slides upon which a biological sample has been mounted so that a cartridge and a slide form a single unit; an mechanism within the instrument for processing said one or more slides or one or more cartridges; a mechanism within the instrument for extracting biological material from the biological samples on the one or more slides or one or more cartridges;
a processor within the instrument which may control deposition of extracted biological materials from one or more biological samples into individual receptacles; a mechanism within the instrument for depositing extracted biological materials from one or more biological samples into individual receptacles; a mechanism within the instrument that mechanically or pneumatically or electrically inserts the individual receptacles into a device for purifying biological material, including tissue, cells, nucleotides, or proteins, and wherein the instrument and the device for purifying biological material are integrated as a single unit or exist as separate units which are interfaced by automatic means; a mechanism within the device for purifying biological material that mechanically or pneumatically or electrically transfers the extracted biological material to an analytical device, wherein the analytical device may conduct analyses comprising genetic or protein analysis.

In another embodiment, we disclose a device for scientific analysis of purified and extracted biological material from a biological sample, the device comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism by which each slide or cartridge is assigned a tag, wherein said tag comprises a sample or patient specific identifier; a mechanism by which the location, status, and processing of each slide or cartridge can be tracked through the process via use of the assigned tag of each slide or cartridge; a reader in the instrument, wherein the reader will assign images to each sample before and after extraction of biological material from the sample, wherein such images may comprise morphology images of the sample; a mechanism within the instrument for extracting biological material from the biological samples on the one or more slides or one or more cartridges, wherein the mechanism may operate by manual, automatic or robotic means; a mechanism within the instrument for depositing the extracted biological material in one or more individual receptacles; a mechanism within the instrument that mechanically or pneumatically or electrically inserts the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; a mechanism within the device for purifying biological material that mechanically or pneumatically or electrically transfers the extracted biological material to an analytical device, wherein the analytical device may conduct analyses comprising image analysis; a network connection to a computer database that may display medical information derived from the image analysis. Further embodiments disclose the device, wherein the analytical device may associate images of samples before and after extraction of biological material; the device, wherein the individual receptacles may be tagged and tracked through the process; the device, wherein the computer code necessary to track tagged samples or receptacles through the process is contained within the device; the device, wherein the tags may comprise colored tags, RF tags, mechanical tags, or electrical tags; the device, wherein the tagged receptacles may be tracked through analyses that comprise genetic screening, protein screening, drug or therapy screens, or live cell culture screens; the device, wherein the image analysis overlays images of samples before and after extraction of biological material; the device, wherein the images may be electronically tagged and tracked, and wherein the information displayed from overlaying images may be stored in a computer database; the device, wherein medical information derived from the image analysis is communicated by a network connection to a computer database that comprises patient records; the device, wherein the device may be operated by a user over a network connection that is linked to the device; the device, wherein the analytical device may display information that follows the progress of a patient through disease diagnosis and treatment; the device, wherein a patient who has previously had one or more biological samples processed by the device may have a new set of one or more biological samples processed by the device, and wherein the biological samples taken previously and the new biological samples may be tracked by a patient-specific identifier stored in a computer database along with the images taken of all said biological samples, and wherein images of the biological samples taken previously and the new biological samples may be associated by means comprising overlaying or animation so that differences in the images may be recognized; the device, wherein the analytical device is network connected to a computer database that retains all information derived from processing biological samples, and wherein said computer database may be accessed by a network connection by users; the device, wherein the analytical device is network connected to a computer database that retains all information derived from processing biological samples, and wherein said computer database is network connected to existing disease and pathology databases.

In another embodiment, we disclose a method for purifying and extracting biological material from a biological sample for scientific analysis, the method comprising: inserting one or more slides or one or more cartridges into an instrument for processing said slide or cartridges, wherein a biological sample has been mounted on the one or more slides, or wherein the one or more cartridges have been attached to one or more slides upon which a biological sample has been mounted so that a cartridge and a slide form a single unit; extracting biological material from the biological samples on the one or more slides or one or more cartridges, wherein the extracting may operate by manual, automatic or robotic means within the instrument; aligning the placement of an individual receptacle for extracted biological material with the placement of each slide or cartridge within the instrument; depositing the extracted biological material in one or more individual receptacles; inserting the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; purifying the extracted biological material within the individual receptacles; transferring the purified and extracted biological material to an analytical device by mechanical, pneumatic or electrical means, wherein the extracted biological material within the individual receptacles is made available for analysis by the analytical device, wherein the analytical device may conduct analyses comprising image analysis; displaying medical information derived from the image analysis, wherein the medical information is communicated through a network connection to a computer database. Further embodiments disclose the method, wherein the image analysis comprises displaying diagnostic and treatment information; the method, wherein the image analysis comprises linking by a network connection to information contained in computer databases comprising information from morphology, genetic screens, protein screens, or biomolecules correlated to disease; the method, wherein the image analysis comprises accessing computer code that enables the display of medical information, wherein said medical information comprises diagnostic or treatment information; the method, wherein the image analysis comprises displaying additional metrics comprising: 1) percent cells with expressed antibody that is indicative of a type of cancer and that would bind to a substrate and be made visible; and 2) genes that are correlated with that type of cancer; the method, wherein the image analysis comprises displaying layered information, wherein said layered information comprises information regarding morphology, genes, or live cell responses.

In another embodiment, we disclose a device for scientific analysis of purified and extracted biological material from a biological sample, the device comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in one or more individual receptacles; a mechanism within the instrument that mechanically or pneumatically or electrically inserts the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; a mechanism within the device for purifying biological material that mechanically or pneumatically or electrically transfers the extracted biological material to an analytical device, wherein the analytical device may conduct analyses comprising image analysis; a network connection to a computer database that may display medical information derived from the image analysis. Further embodiments disclose the device, wherein the medical information displayed includes diagnostic and treatment information; the device, wherein information derived from the image analysis is linked by a network connection to information contained in computer databases comprising information from morphology, genetic screens, protein screens, or bio-molecules correlated to disease; the device, wherein the analytical device comprises computer code that enables the display of medical information, wherein said medical information comprises diagnostic or treatment information; the device, wherein the device may display additional metrics comprising: 1) percent cells with expressed antibody that is indicative of a type of cancer and that would bind to a substrate and be made visible; and 2) genes that are correlated with that type of cancer; the device, wherein the device may display layered information comprising information regarding morphology, genes, or live cell responses.

In another embodiment, we disclose a method for purifying and extracting biological material from a biological sample for scientific analysis, the method comprising: inserting one or more slides or one or more cartridges into an instrument for processing said slide or cartridges, wherein a biological sample has been mounted on the one or more slides, or wherein the one or more cartridges have been attached to one or more slides upon which a biological sample has been mounted so that a cartridge and a slide form a single unit; extracting biological material from the biological samples on the one or more slides or one or more cartridges, wherein the extracting may operate by manual, automatic or robotic means within the instrument; aligning the placement of an individual receptacle for extracted biological material with the placement of each slide or cartridge within the instrument; depositing the extracted biological material in one or more individual receptacles; inserting the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; purifying the extracted biological material within the individual receptacles; transferring the purified and extracted biological material to an analytical device by mechanical, pneumatic or electrical means, wherein the extracted biological material within the individual receptacles is made available for analysis by the analytical device, wherein the analytical device may conduct analyses comprising image analysis. Further embodiments disclose the method, wherein the image analysis comprises overlaying different images taken from biological samples derived from a single patient; the method, wherein the image analysis makes available information that enables an estimate of the amount of biological material extracted from the biological sample; the method, wherein the image analysis comprises overlaying different images that may be distinguished by means comprising transparent colors, animated layers, a three-dimensional layered image, or a clickable image; the method, wherein the image analysis comprises displaying information that provides a estimation of the extent of tumors in biological samples derived from a cancer patient; the method, wherein the image analysis comprises displaying an overlay of protein, antibody, or other scientific information overlaid on the different images taken from the biological samples; the method, wherein the image analysis comprises displaying information that provides indications that where certain genes are expressed in a region of certain cells then therapeutic drugs are able to treat those cells; the method, wherein the image analysis comprises displaying information that indicates that certain therapeutic drugs will be effective to treat certain regions of a tumor in biological samples derived from a cancer patient.

In another embodiment, we disclose a device for scientific analysis of purified and extracted biological material from a biological sample, the device comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in one or more individual receptacles; a mechanism within the instrument that mechanically or pneumatically or electrically inserts the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; a mechanism within the device for purifying biological material that mechanically or pneumatically or electrically transfers the extracted biological material to an analytical device, wherein the analytical device may conduct analyses comprising image analysis. Further embodiments disclose the device, wherein the analytical device may display an overlay of different images taken from biological samples derived from a single patient; the device, wherein the analytical device may display information that provides an estimate of the amount of biological material extracted from the biological sample; the device, wherein the analytical device may display information overlaid on another image by means comprising transparent colors, animated layers, a three-dimensional layered image, or a clickable image; the device, wherein the analytical device may display information that provides a estimation of the extent of tumors in biological samples derived from a cancer patient; the device, wherein the analytical device may display an overlay of protein, antibody, or other scientific information overlaid on the different images taken from the biological samples; the device, wherein the analytical device may display information that provides indications that where certain genes are expressed in a region of certain cells then therapeutic drugs are able to treat those cells; the device, wherein the analytical device may display information that indicates that certain therapeutic drugs will be effective to treat certain regions of a tumor in biological samples derived from a cancer patient.

In another embodiment, we disclose a method for analysis of extracted biological material from a subject, the method comprising: taking one or more biological samples from a subject; transferring said one or more biological samples to one or more slides or one or more cartridges, wherein a biological sample has been mounted on the one or more slides, or wherein the one or more cartridges have been attached to one or more slides upon which a biological sample has been mounted so that a cartridge and a slide form a single unit; inserting one or more slides or one or more cartridges into an instrument for processing said slide or cartridges; extracting biological material from the biological samples on the one or more slides or one or more cartridges, wherein the extracting may operate by manual, automatic or robotic means within the instrument; depositing different extracted biological materials from one or more biological samples into a single individual receptacle; inserting the single individual receptacle into an analytical device, wherein the instrument and the analytical device are integrated as a single unit or exist as separate units which are interfaced by manual, semi-automatic or robotic means, and wherein the analytical device may conduct analyses comprising genetic or protein analysis. Further embodiments disclose the method, wherein each biological sample taken from a subject is tracked by means comprising radio-frequency tags, colored markings, mechanical tabs or a computer database.

In another embodiment, we disclose a device for analysis of extracted biological material from a subject, the device comprising: an instrument for taking one or more biological samples from a subject; a mechanism for transfer of a biological sample to one or more slides or one or more cartridges, wherein a biological sample has been mounted on the one or more slides, or wherein the one or more cartridges have been attached to one or more slides upon which a biological sample has been mounted so that a cartridge and a slide form a single unit; an instrument for processing said one or more slides or one or more cartridges; a mechanism within the instrument for extracting biological material from the biological samples on the one or more slides or one or more cartridges, wherein the mechanism may operate by manual, automatic or robotic means; a processor within the instrument which may control deposition of different extracted biological materials from one or more biological samples into a single individual receptacle; a mechanism within the instrument for depositing different extracted biological materials from one or more biological samples into a single individual receptacle; a mechanism within the instrument that mechanically or pneumatically or electrically inserts the single individual receptacle into an analytical device, wherein the instrument and the analytical device are integrated as a single unit or exist as separate units which are interfaced by manual, semi-automatic or robotic means, and wherein the analytical device may conduct analyses comprising genetic or protein analysis. Further embodiments disclose the device, wherein each biological sample taken from a subject is tracked by means comprising radio-frequency tags, colored markings, mechanical tabs or a computer database.

In another embodiment, we disclose a method for analysis of gene expression in extracted biological material from a cancer patient, the method comprising: incorporating cancer genes from a patient into living cells so that the cancer genes are expressed; transferring a biological sample comprising said living cells that express cancer genes from a patient to one or more slides or one or more cartridges, wherein a biological sample has been mounted on the one or more slides, or wherein the one or more cartridges have been attached to one or more slides upon which a biological sample has been mounted so that a cartridge and a slide form a single unit; inserting one or more slides or one or more cartridges into an instrument for processing said slide or cartridges; extracting biological material from the biological samples on the one or more slides or one or more cartridges, wherein the extracting may operate by manual, automatic or robotic means within the instrument; depositing different extracted biological materials into one or more different individual receptacles; inserting the one or more different individual receptacles into an analytical device, wherein the instrument and the analytical device are integrated as a single unit or exist as separate units which are interfaced by manual, semi-automatic or robotic means, and wherein the analytical device may conduct analyses comprising comparative analysis of the properties of different extracted biological material deposited in the one or more different individual receptacles. Further embodiment disclose the method, wherein the different extracted biological materials are from a biological sample from a single patient.

In another embodiment, we disclose a device for analysis of gene expression in extracted biological material from a cancer patient, the device comprising: an instrument for incorporating cancer genes from a patient into living cells so that the cancer genes are expressed; a mechanism for transfer of a biological sample comprising said living cells that express cancer genes from a patient to one or more slides or one or more cartridges, wherein a biological sample has been mounted on the one or more slides, or wherein the one or more cartridges have been attached to one or more slides upon which a biological sample has been mounted so that a cartridge and a slide form a single unit; an instrument for processing said one or more slides or one or more cartridges; a mechanism within the instrument for extracting biological material from the biological samples on the one or more slides or one or more cartridges, wherein the mechanism may operate by manual, automatic or robotic means; a processor within the instrument which may control deposition of different extracted biological materials into one or more different individual receptacles; a mechanism within the instrument for depositing the extracted biological material in one or more different individual receptacles; a mechanism within the instrument that mechanically or pneumatically or electrically inserts the one or more different individual receptacles into an analytical device, wherein the instrument and the analytical device are integrated as a single unit or exist as separate units which are interfaced by manual, semi-automatic or robotic means, and wherein the analytical device may conduct analyses comprising comparative analysis of the properties of different extracted biological material deposited in the one or more different individual receptacles. Further embodiments disclose the device, wherein the different extracted biological materials are from a biological sample from a single patient; the device, wherein the instrument for processing said one or more slides or one more cartridges may comprise a layer for extracting biological materials and a layer for conducting analysis of extracted biological materials; the device, wherein the layer for conducting analysis of extracted biological materials may provide up to three or more different individual receptacles for depositing of the extracted biological materials to be made available for analysis.

In another embodiment, we disclose a method for purifying and extracting biological material from a biological sample for scientific analysis, the method comprising: inserting one or more slides or one or more cartridges into an instrument for processing said slide or cartridges, wherein a biological sample has been mounted on the one or more slides, or wherein the one or more cartridges have been attached to one or more slides upon which a biological sample has been mounted so that a cartridge and a slide form a single unit; extracting biological material from the biological samples on the one or more slides or one or more cartridges, wherein the extracting may operate by manual, automatic or robotic means within the instrument; aligning the placement of an individual receptacle for extracted biological material with the placement of each slide or cartridge within the instrument; depositing the extracted biological material in one or more individual receptacles; inserting the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; purifying the extracted biological material within the individual receptacles; transferring the purified and extracted biological material to an analytical device by mechanical, pneumatic or electrical means, wherein the extracted biological material within the individual receptacles is made available for analysis by the analytical device, wherein the analytical device may conduct analyses comprising cell culture analysis.

In another embodiment, we disclose a device for scientific analysis of purified and extracted biological material from a biological sample, the device comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in one or more individual receptacles; a mechanism within the instrument that mechanically or pneumatically or electrically inserts the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; a mechanism within the device for purifying biological material that mechanically or pneumatically or electrically transfers the extracted biological material to an analytical device, wherein the analytical device may conduct analyses comprising cell culture analysis.

In another embodiment, we disclose a method for purifying and extracting biological material from a biological sample for scientific analysis, the method comprising: inserting one or more slides or one or more cartridges into an instrument for processing said slide or cartridges, wherein a biological sample has been mounted on the one or more slides, or wherein the one or more cartridges have been attached to one or more slides upon which a biological sample has been mounted so that a cartridge and a slide form a single unit; extracting biological material from the biological samples on the one or more slides or one or more cartridges, wherein the extracting may operate by manual, automatic or robotic means within the instrument; aligning the placement of an individual receptacle for extracted biological material with the placement of each slide or cartridge within the instrument; depositing the extracted biological material in one or more individual receptacles; inserting the individual receptacles into a device for purifying biological material, including tissue, cells, nucleotides, or proteins, and wherein the instrument and the device for purifying biological material are integrated as a single unit or exist as separate units which are interfaced by manual, semi-automatic or robotic means; purifying the extracted biological material within the individual receptacles; transferring the purified and extracted biological material to an analytical device by mechanical, pneumatic or electrical means, wherein the extracted biological material within the individual receptacles is made available for analysis by the analytical device, wherein the analytical device may conduct analyses comprising drug screening or genetic screening of the purified and extracted biological material. Further embodiments disclose the method, wherein a single individual receptacle containing extracted biological material is processed by both the device for purifying biological material and the analytical device.

In another embodiment, we disclose a method for extracting biological material from a biological sample for genetic analysis, the method comprising: inserting one or more slides or one or more cartridges into an instrument for processing said slide or cartridges, wherein a biological sample has been mounted on the one or more slides, or wherein the one or more cartridges have been attached to one or more slides upon which a biological sample has been mounted so that a cartridge and a slide form a single unit; extracting biological material from the biological samples on the one or more slides or one or more cartridges, wherein the extracting may operate by manual, automatic or robotic means within the instrument; aligning the placement of an individual receptacle for extracted biological material with the placement of each slide or cartridge within the instrument; depositing the extracted biological material in one or more individual receptacles; inserting the individual receptacles into a genetic screening device by mechanical, pneumatic or electrical means, wherein the extracted biological material within the individual receptacles is made available for analysis by the genetic screening device.

In another embodiment, we disclose a device for genetic analysis of extracted biological material from a biological sample, the device comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in one or more individual receptacles; a mechanism within the instrument that mechanically or pneumatically or electrically inserts the individual receptacles into a genetic screening device, wherein the instrument and the genetic screening device are spatially arranged so that placement of each slide or cartridge within the instrument is aligned with the placement of an individual receptacle for extracted biological material.

In another embodiment, we disclose a method for extracting biological material from a biological sample for scientific analysis, the method comprising: obtaining a biological sample from a subject; mounting the biological sample on a slide; optionally, attaching the slide to a cartridge so that the slide and cartridge form a single unit; inserting the slide or cartridge into an instrument for processing one or more slides or one or more cartridges; processing the one or more slides or one or more cartridges to extract biological material from the biological samples within the instrument by manual, automatic or robotic means; depositing the extracted biological material within the instrument in a position that makes the extracted biological material available for scientific analysis; transferring the extracted biological material by manual, semi-automatic or robotic means to an analytical device, wherein the analytical device performs a scientific analysis of the extracted biological material, including genetic screening or protein screening. Further embodiments disclose the method, wherein the analytical device is integrated with the instrument so that the analytical device and the instrument form a single unit; the method, wherein the analytical device is a separate device which interfaces with the instrument by manual, semi-automatic or robotic means; the method, wherein the scientific analysis is a clinical analysis or a pathology analysis.

In another embodiment, we disclose a system for extracting biological material from a biological sample for scientific analysis, the system comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in a position within the instrument that makes the extracted biological material available for scientific analysis; an analytical device that interfaces with the instrument so that the extracted biological material is transferred by manual, semi-automatic or robotic means to the analytical device, wherein the analytical device performs the scientific analysis, including genetic screening or protein screening.

In another embodiment, we disclose a system for extracting biological material from a biological sample for scientific analysis, the system comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in a position within the instrument that makes the extracted biological material available for scientific analysis; an analytical device that is integrated with the instrument so that the analytical device and the instrument form a single unit, wherein the analytical device performs the scientific analysis, including genetic screening or protein screening.

In another embodiment, we disclose a system for extracting biological material from a biological sample for scientific analysis, the system comprising: an instrument for processing one or more slides or one or more cartridges, wherein a biological sample has been mounted on the one or more slides, or wherein the one or more cartridges have been attached to one or more slides upon which a biological sample has been mounted so that a cartridge and a slide form a single unit; a mechanism within the instrument for extracting biological material from the biological samples on the one or more slides or one or more cartridges, wherein the mechanism may operate by manual, automatic or robotic means; a mechanism within the instrument for depositing the extracted biological material in a position within the instrument that makes the extracted biological material available for scientific analysis. Further embodiments disclose the system, wherein the extracted biological material is made available for genetic screening, including screening of nucleotides, DNA and mRNA; the system, wherein the extracted biological material is made available for protein screening; the system, wherein scientific analysis is conducted within the instrument itself or by one or more separate analytical devices with which the instrument is interfaced.

In another embodiment, we disclose a slide processing system for extracting biological material from one or more biological samples, the system comprising: a carousel, wherein said carousel contains one or more slots into which one or more slides upon which a biological sample is mounted may be placed by manual or automated or robotic means; a mechanism of rotation for the carousel, wherein said one or more slides are rotated to move through an ordered series of positions on the carousel; a first position on the carousel, wherein a slide has a film pressed against the biological sample mounted on the slide, and wherein the film comprises a substrate suitable for extracting biological material from the biological sample, and wherein the film may be imaged; a second position on the carousel, wherein the film may be activated so that biological material desired for extraction from the biological sample adheres to the film; a third position on the carousel, wherein the film may be removed from pressing against the biological sample by manual or automated or robotic means; a fourth position on the carousel, wherein the film may be reimaged; a fifth position on the carousel, wherein the film may be deposited into a receptacle for further analysis of the extracted biological material. Further embodiments disclose the slide processing system, wherein an analysis of the extracted biological material comprises depositing the extracted biological material on one or more individual receptacles within the carousel, or in another instrument that is interfaced with the carousel.

In another embodiment, we disclose a cartridge processing system for extracting biological material from one or more biological samples, the system comprising: a carousel, wherein said carousel contains one or more slots into which one or more cartridges containing biological samples may be placed; a mechanism of rotation for the carousel, wherein said one or more cartridges are rotated to enter inside a device, and wherein said device operates a sealing mechanism, wherein the sealing mechanism may seal the device and the cartridge by mechanical, hydraulic, or electrical means, or by the imposition of a vacuum; a timing mechanism which controls the period of time for which the device and the cartridge is sealed by the sealing mechanism, wherein once the period of time for which the device and the cartridge are sealed is elapsed, the cartridge will be rotated by the carousel out of the device. Further embodiments disclose the cartridge processing system, wherein the mechanism of rotation may operate by manual or automated or robotic means; the cartridge processing system, cartridges are placed on or removed from the carousel by manual or automated or robotic means; the cartridge processing system, wherein the cartridges may be illuminated or imaged while inserted into the slots of the carousel; the cartridge processing system, wherein the cartridges are assembled prior to processing by manual, automated or robotic means by a method comprising: acquiring the biological sample, orienting the biological sample to the cartridge backing or orienting the cartridge backing to the biological sample, pressing a film pre-loaded on the cartridge against the biological sample, and then sealing the cartridge by manual, automated or robotic means; the cartridge processing system, wherein the biological samples may be tissue sections, whole tissue samples, histology slide, biopsy material or samples, frozen or fixed (e.g., formalin, paraffin, or ethanol fixed) samples, cellular specimens or cellular preparation, cell smears, cytology preparations; the cartridge processing system, wherein films are attached to the cartridge backing by stamping, rolling, or other types of applied pressure, by shrink sealing, or by other mechanical or chemical means; the cartridge processing system, wherein the cartridges are supplied with a kit containing reagents necessary for the extraction of biological material from a biological sample by the cartridge, wherein the kit may comprise optical, electromagnetic, or heat activated molecules, chemicals, biomolecules, liquid or solid reagents, ligands, antibodies, fusion molecules, polymers, visualizing agents, proteins, DNA, mRNA, enzymes, lipids, and carbohydrates; the cartridge processing system, wherein the extracted biological material may be deposited in individual receptacles positioned underneath the carousel.

In another embodiment, we disclose a cartridge processing system for extracting biological material from one or more biological samples, the system comprising: a table-top platform, wherein said table-top platform comprises a mechanism for conveying inside a device a cartridge containing a biological sample; wherein said device operates a sealing mechanism, wherein the sealing mechanism may seal the device and the cartridge by mechanical, hydraulic, or electrical means, or by the imposition of a vacuum; a timing mechanism which controls the period of time for which the device and the cartridge is sealed by the sealing mechanism, wherein once the period of time for which the device and the cartridge are sealed is elapsed, the cartridge will be conveyed out of the device. Further embodiments disclose the cartridge processing system, wherein the timing mechanism activates an auditory or visual signal when the period of time for which the device and cartridge are sealed by the sealing mechanism ends; the cartridge processing system, wherein cartridges are placed on or removed from the table-top platform by manual or automated or robotic means.

In another embodiment, we disclose a cartridge processing system for extracting biological material from one or more biological samples, the system comprising: a cartridge-processing instrument, wherein said cartridge-processing instrument comprises a top half and a bottom half linked by a hinged mechanism; said bottom half forming a stage for placement of one or more cartridges upon which are mounted biological samples; said top half forming a lid, wherein said lid may be closed over the cartridges so that the cartridges are fully enclosed by the cartridge-processing instrument; a film adhered to said bottom half, wherein said film comprises a substrate suitable for extracting biological material from biological samples mounted on the cartridges, and wherein said film is also adhered to said top half so that closing the lid over the one or more cartridges presses the film against the one or more biological samples; a space when the lid of the cartridge-processing instrument is open so that the cartridges may be positioned inside the instrument by manual or automated or robotic means; a sealing mechanism for the cartridge-processing instrument, wherein the sealing mechanism may seal the instrument and the film pressed against the cartridges by mechanical, hydraulic, or electrical means, or by the imposition of a vacuum. Further embodiments disclose the cartridge processing system, wherein the system further comprises a timing mechanism which controls the period of time for which the table-top platform is sealed by the sealing mechanism; the cartridge processing system, wherein the timing mechanism activates an auditory or visual signal when the period of time for which the table-top platform is sealed by the sealing mechanism ends; the cartridge processing system, wherein an analysis of the extracted biological material comprises depositing the extracted biological material on one or more individual receptacles within the table-top platform, or in another instrument that is interfaced with the table-top platform.

In another embodiment, we disclose a slide processing system for extracting biological material from one or more biological samples, the system comprising: a slide-processing instrument, wherein said slide-processing instrument comprises a top half and a bottom half linked by a hinged mechanism; said bottom half forming a stage for placement of one or more slides upon which are mounted biological samples; said top half forming a lid, wherein said lid may be closed over the slides so that the slides are fully enclosed by the slide-processing instrument; a film adhered to said bottom half, wherein said film comprises a substrate suitable for extracting biological material from biological samples mounted on the slides, and wherein said film is also adhered to said top half so that closing the lid over the one or more slides presses the film against the one or more biological samples; a space when the lid of the slide-processing instrument is open so that the slides may be positioned inside the instrument by manual or automated or robotic means; a sealing mechanism for the slide-processing instrument, wherein the sealing mechanism may seal the instrument and the film pressed against the slides by mechanical, hydraulic, or electrical means, or by the imposition of a vacuum. Further embodiments disclose the slide processing system, wherein the system further comprises a timing mechanism which controls the period of time for which the slide-processing instrument is sealed by the sealing mechanism; the slide processing system, wherein the timing mechanism activates an auditory or visual signal when the period of time for which the slide-processing instrument is sealed by the sealing mechanism ends; the slide processing system, wherein an analysis of the extracted biological material comprises depositing the extracted biological material on one or more individual receptacles within the table-top platform, or in another instrument that is interfaced with the table-top platform.

In another embodiment, we disclose a slide processing system for extracting biological material from one or more biological samples, the system comprising: a table-top platform, wherein said table-top platform comprises a top half and a bottom half linked by a hinged mechanism; said bottom half forming a stage for placement of one or more slides upon which are mounted biological samples; said top half forming a lid, wherein said lid may be closed over the one or more slides so that the slides are fully enclosed by the table-top platform; a film attached to the lid, wherein said film comprises a substrate suitable for extracting biological material from biological samples mounted on the slides, and wherein closing the lid over the one or more slides presses the film against the one or more biological samples; a sealing mechanism for the table-top platform, wherein the sealing mechanism may seal the platform and the film pressed against the slides by mechanical, hydraulic, or electrical means, or by the imposition of a vacuum. Further embodiments disclose the slide processing system, wherein the system further comprises a timing mechanism which controls the period of time for which the table-top platform is sealed by the sealing mechanism; the slide processing system, wherein the timing mechanism activates an auditory or visual signal when the period of time for which the table-top platform is sealed by the sealing mechanism ends.

In another embodiment, we disclose a cartridge processing system for extracting biological material from one or more biological samples, the system comprising: a table-top platform, wherein said table-top platform comprises a top half and a bottom half linked by a hinged mechanism; said bottom half forming a stage for placement of one or more cartridges containing biological samples; said top half forming a lid, wherein said lid may be closed over the one or more cartridges so that the cartridges are fully enclosed by the table-top platform; a sealing mechanism for the table-top platform, wherein the sealing mechanism may seal the platform and the cartridges by mechanical, hydraulic, or electrical means, or by the imposition of a vacuum. Further embodiments disclose the cartridge processing system, wherein the system further comprises a timing mechanism which controls the period of time for which the table-top platform is sealed by the sealing mechanism; the cartridge processing system, wherein the timing mechanism activates an auditory or visual signal when the period of time for which the table-top platform is sealed by the sealing mechanism ends; the cartridge processing system, wherein the extracted biological material is deposited in an individual receptacle for analysis, wherein such analysis is conducted either within a separate layer of the table-top platform or within a separate instrument with which the table-top platform is interfaced; the cartridge processing system, wherein the separate instrument conducts DNA analysis of the extracted biological material; the cartridge processing system, wherein the separate instrument conducts drug screening of the extracted biological material; the cartridge processing system, extracted biological materials from more than one biological sample may be deposited into the same receptacle for analysis.

In another embodiment, we disclose a kit for extracting biological material from a biological sample, comprising: a slide, wherein the biological sample may be mounted on the slide; a cartridge, wherein the slide upon which the biological sample may be attached to the cartridge to form a single unit; a film, wherein the cartridge is pre-loaded with the film, said film comprising a substrate suitable for extracting biological material from the biological sample.

In another embodiment, we disclose a method of extracting biological material from a biological sample, comprising: mounting a biological sample upon a slide; attaching the slide to a cartridge that contains a pre-loaded film, wherein the film comprises a substrate suitable for extracting biological material from the biological sample; pressing the film against the biological sample mounted upon the slide; ending the pressing of the film against the biological sample mounted upon the slide; removing the film from the cartridge by using a pull tab attached to the film; extracting biological material from the biological sample that has been adhered to the film. Further embodiments disclose the method, wherein attaching the slide to a cartridge that contains a pre-loaded film, comprises inserting the slide into grooves in the cartridge that enable the cartridge and slide form a single unit, wherein the entire slide is fully enclosed by the cartridge; the method, wherein attaching the slide to a cartridge that contains a pre-loaded film, comprises inserting the slide into grooves in the cartridge that enable the cartridge and slide form a single unit, wherein the slide is only partially enclosed by the cartridge; the method, wherein pressing the film against the biological sample mounted upon the slide, comprises closing a hinged mechanism which links a top half of the cartridge to a bottom half of the cartridge, wherein the top half of the cartridge may contain the film, and the bottom half of the cartridge may contain the slide upon which the biological sample has been mounted; the method, wherein ending the pressing of the film against the biological sample, comprises opening a hinged mechanism which links a top half of the cartridge to a bottom half of the cartridge, wherein the top half of the cartridge may contain the film, and the bottom half of the cartridge may contain the slide upon which the biological sample has been mounted; the method, wherein pressing the film against the biological sample mounted upon the slide, comprises adjusting a link between a top half of the cartridge and a bottom half of the cartridge, wherein the top half of the cartridge may contain the film, and the bottom half of the cartridge may contain the slide upon which the biological sample has been mounted, and wherein when the link is adjusted so that the top half of the cartridge forms a single unit with the bottom half of the cartridge the film will be pressed against the biological sample mounted on the slide; the method, wherein ending the pressing the film against the biological sample mounted upon the slide, comprises adjusting a link between a top half of the cartridge and a bottom half of the cartridge, wherein the top half of the cartridge may contain the film, and the bottom half of the cartridge may contain the slide upon which the biological sample has been mounted, and wherein when the link is adjusted so that the top half of the cartridge no longer forms a single unit with the bottom half of the cartridge the film will be no longer be pressed against the biological sample mounted on the slide; the method, wherein pressing the film against the biological sample mounted upon the slide, comprises pressing by a device into which the cartridge has been inserted, wherein the device presses the film by mechanical, hydraulic, or electrical means, or by the imposition of a vacuum; the method, wherein pressing the film against the biological sample mounted upon the slide, comprises triggering a switch on the cartridge or on a device into which the cartridge has been inserted; the method, wherein removing the film from the cartridge via a pull tab, comprises manual pulling on the pull tab, or automatic pulling on the pull tab by a device into which the cartridge has been inserted; the method, wherein extracting the biological material from the film, comprises dissolving the film or removing the biological material that is adhering to the film.

In another embodiment, we disclose a cartridge for extracting biological material from a biological sample, the cartridge comprising: a film pre-loaded on the cartridge, wherein the film comprises a substrate suitable for extracting biological material from the biological sample; an adjustable link for attaching the cartridge to a slide upon which the biological sample has been mounted, wherein the cartridge and slide form a single unit after attaching the cartridge to the slide; a mechanism for pressing the film against the biological sample mounted on the slide when the slide is attached to the cartridge; a mechanism for ending the pressing of the film against the biological sample mounted on the slide when the slide is attached to the cartridge; a pull tab which is attached to the film, wherein the pull tab enables the film to be removed from the cartridge. Further embodiments disclose the cartridge, wherein the adjustable link for attaching the cartridge to the slide upon which the biological sample has been mounted, comprises hooks or grooves that enable attachment of the cartridge to the corners of the slide; the cartridge, wherein the adjustable link for attaching the cartridge to the slide upon which the biological sample has been mounted, comprises a groove which enables the entire slide to be fully enclosed by the cartridge when the film is pressing against the biological sample mounted on the slide; the cartridge, wherein the adjustable link for attaching the cartridge to the slide upon which the biological sample has been mounted, comprises a groove which enables the slide to be attached to the cartridge by three or fewer sides of the slide; the cartridge, wherein the mechanism for pressing the film against the biological sample mounted on the slide when the slide is attached to the cartridge, comprises a hinged mechanism which links a top half of the cartridge to a bottom half of the cartridge, wherein the top half of the cartridge may contain the film, and the bottom half of the cartridge may contain the slide upon which the biological sample has been mounted, and wherein closing the hinged mechanism will press the film against the biological sample mounted on the slide; the cartridge, wherein the mechanism for ending the pressing of the film against the biological sample mounted on the slide, comprises opening the hinged mechanism so that the film no longer presses against the biological sample mounted on the slide; the cartridge, wherein the mechanism for pressing the film against the biological sample mounted on the slide when the slide is attached to the cartridge, is an adjustable link between a top half of the cartridge and a bottom half of the cartridge, wherein the top half of the cartridge may contain the film, and the bottom half of the cartridge may contain the slide upon which the biological sample has been mounted, and wherein when the link is adjusted so that the top half of the cartridge forms a single unit with the bottom half of the cartridge the film will be pressed against the biological sample mounted on the slide; the cartridge, wherein the mechanism for ending the pressing of the film against the biological sample mounted on the slide, comprises adjusting the link between the top half of the cartridge and the bottom half of the cartridge so that the top half and the bottom half no longer form a single unit; the cartridge, wherein the mechanism for pressing the film against the biological sample mounted on the slide, comprises triggering a switch on the cartridge or on a device into which the cartridge has been inserted; the cartridge, wherein the slide upon which a biological sample is mounted is a backing that is more rigid than the sample, and the film pressing against the biological sample is less rigid than the sample; the cartridge, wherein the cartridge is disposable after being used to extract biological material from a biological sample; the cartridge, wherein the cartridge is re-usable after being used to extract biological material from a biological sample; the cartridge, wherein a material forming the film comprises polymer, polystyrene, wax, rubber, silicon, silicone, paper, cloth, metal, alloys, an impregnated web, or a liquid material that dries or otherwise hardens to form a flexible, semi-flexible, or rigid covering; the cartridge, wherein a material forming the cartridge comprises glass, silicon, polymer, polystyrene, plastic, rubber, paper, wood, metal, or alloys; the cartridge, wherein the cartridge comprises rigid, semi-rigid or flexible layers; the cartridge, wherein the film is readily dissolvable; the cartridge, wherein the film is a substrate which enables biological material attached to the substrate to be readily removed from the substrate; the cartridge, wherein the cartridge enables the film to be imaged before the film is pressed against the biological sample mounted on the slide, or imaged while the film is pressed against the biological sample mounted on the slide, or imaged after the film is pressed against the biological sample mounted on the slide; the cartridge, wherein the film pressed against the biological sample mounted on the slide may be pressed by a device into which the cartridge has been inserted, wherein the device presses the film by mechanical, hydraulic, or electrical means, or by the imposition of a vacuum; the cartridge, wherein the pull tab which enables the film to be removed from the cartridge, may be pulled on manually or automatically by a device into which the cartridge has been inserted.

Further aspects and advantages of the invention will appear from the following description taken together with the accompanying drawings.

BRIEF DESCRIPTION OF THE DRAWINGS

The above and other objects and advantages of the invention will be apparent upon consideration of the following detailed description, taken in conjunction with the accompanying figure, in which like reference characters refer to like parts throughout, and in which:

FIG. 2A is a view of another preferred embodiment of the invention, a reusable cartridge that is designed to receive a microscope slide upon which a biological sample has been mounted. FIG. 2B shows the cartridge with the slide inserted and contained within the cartridge.

DETAILED DESCRIPTION OF THE EXEMPLARY EMBODIMENTS

One mode for carrying out the invention is presented in terms of its preferred embodiment, herein depicted within FIG. 1. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the claims. As used throughout this application, the word may is used in a permissive sense (i.e., meaning having the potential to), rather than the mandatory sense (i.e., meaning must). The terms "a" and "an" herein do not denote a limitation of quantity, but rather denote the presence of at least one of the referenced items.

Cartridge Designs

According to the invention, cartridges are designed to allow the extraction of desired regions of the biological sample in a fast and efficient manner, including in a single step. Each cartridge will ensure that a substrate contacts the tissue or biological samples, that the interaction between substrate and the biological samples alters the substrate so that it is focally targeted on the region of interest, and that the alteration is then activated so that the substrate will selectively bind to specific tissue regions, cells, and molecules of interest (e.g., cancer cells from a milieu of many other cells), and will then extract those tissue regions, cells, and molecules of interest.

Figure 1A:
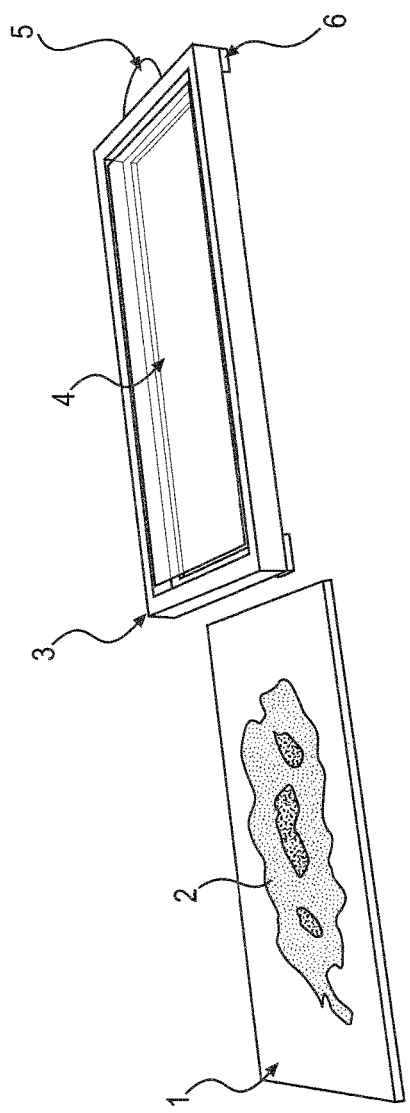
FIG. 1A is a view of a preferred embodiment of the invention, a disposable cartridge that is designed to "snap" over a microscope slide upon which a biological sample has been mounted.
Figure 1B:
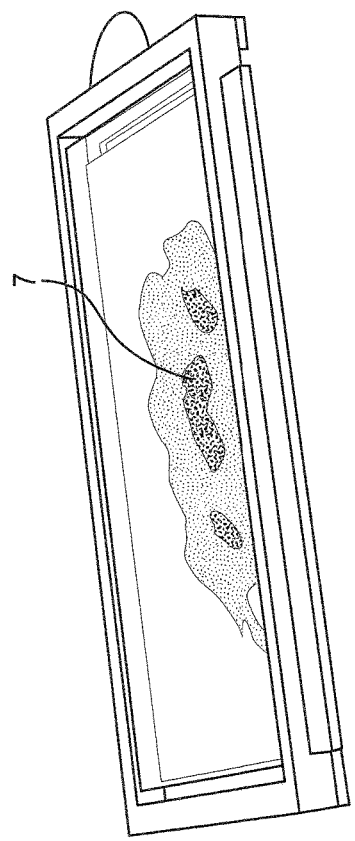
FIG. 1B shows the cartridge snapped into place over the microscope slide.

Referring now to FIG. 1A, one preferred embodiment of the invention is shown in which a cartridge (3), which has been pre-loaded with a film (4) made from a suitable substrate for extracting biological material, is designed to "snap" onto a microscope slide (1) upon which a biological sample (2) has been mounted. The cartridge combines with a slide to form a single unit comprising a biological sample sandwiched between a backing that is more rigid than the sample and a sealing film that is less rigid than the sample. As shown in FIG. 1B, the cartridge is designed to fit over the microscope slide so that the film is pressed (7) against the biological sample mounted on the slide. The size of the cartridges used may vary to suit the sizes of slide available. As shown, each cartridge contains a film which is connected to a pull tab (5) which extends from one end of the cartridge sufficiently far to allow a user to grip the pull tab effectively. The actual mechanism of attaching the cartridge to the slide may be varied in accordance with methods known in the art, such as for example plastic hooks that retain sufficient flexibility to allow the slide to be held in place with the cartridge attached (6), but that will also allow the cartridge to be removed after the extraction process has been completed. The film is attached to the cartridge via means commonly known in the art.

FIG. 1B shows the cartridge and slide attached together in accordance with one preferred embodiment of the invention. The cartridge and slide pressing together combines the biological sample on the slide with the film on the cartridge, which is an optical, electro-magnetic or heat-activated substrate or contains specific molecules that allow desired target regions of the biological sample to be extracted. The film can be laid onto the tissue as the slide is inserted into the cartridge, by for example mechanically, electrically, or optically triggering a mechanism operating within the cartridge, or from outside the cartridge, that presses the film up against the tissue. Pressing can be accomplished by mechanical, hydraulic, or electrical means or preferably by the imposition of a vacuum. Alternatively, after the slide is inserted, a user can press on the cartridge or can activate a button or switch, or the cartridge may be self-activated, to initiate contact between the substrate and the tissue. After a suitable period of time, which may be determined by one of ordinary skill according to the particular kind of extraction being performed, or by a timer or other means, the cartridge is removed from the slide, at which point biological material will also be attached to the film according to the particular extraction technique used. In some embodiments, the cartridge devices of the present application are used for expression micro-dissection, a technique that allows for the procurement of desired cells or tissues via molecular targeting.

Preferably, the sealing film contains or has attached to it an optically or heat activated adherent. The cartridge device is further designed so that the biological sample region, regions, or molecules of interest may be subsequently disassociated from the sealing film. A tab, handle, groove or grooves, the material properties of the film, or a temporary or permanent attachment to the sealing film allows its easy removal from the sample by the user or the parent cartridge processing system into which the cartridge is inserted by the user. For example, the parent system or user removes the film by grasping the pull tab, by pulling the film off using small pins or guides that fit into the grooves, or by a roller that temporarily adheres to the top surface of the flexible sealing film pulling it off. When removed, the sealing film takes with it the desired region, regions or molecules of interest from the biological sample, such as in the case of expression micro-dissection. The pull tab is then pulled on by the user to remove the film from the cartridge. The sealing film may also be removed from the cartridge automatically by mechanical means as part of a larger device into which the cartridge has been inserted for processing. The film may be imaged while pressed on top of the slide, after the initial removal of the cartridge from the slide, or after the film itself is removed from the cartridge by the pull tab. After the film has been removed from the cartridge the film may be further analyzed according to the experimental goals of the user, while the cartridge itself is disposed of. Cartridges in this preferred embodiment are made of disposable plastic or alternative similar materials, which are inexpensive but durable. The material from which the cartridge is made is not limiting upon the invention. The cartridge device is further designed so that the biological sample region, regions, or molecules of interest may be subsequently disassociated from the sealing film.

In preferred embodiments, the sealing film material is chosen/designed so that it can be readily dissolved, or so that its adherence can be reversed releasing the target parts of the biological sample into a chamber or test-tube which forms part of a larger cartridge-processing system. Alternatively, the biological regions or molecules can be scraped off, washed off, or removed by other means inside or outside of a cartridge-processing system.

Examples of the backing materials of the cartridge include, but are not limited to glass, silicon, polymer, polystyrene, plastic, rubber, paper, wood, metal, or alloys. Examples of the sealing film materials include, but are not limited to, polymer, polystyrene, wax, rubber, silicon, silicone, paper, cloth, metal, alloys, an impregnated web, or a liquid material that dries or otherwise hardens to form a flexible, semi-flexible, or rigid covering.

The invention does not depend on a particular embodiment of the cartridge design. For example, in one embodiment the cartridge may be attached on only on one side of the slide, or in another embodiment the cartridge may be designed to contact the slide at all corners of the slide or only on some edges (for example, a C shape that fits around three edges of a slide). The cartridge device may comprise rigid, semi-rigid or flexible layers. The cartridge can be shaped in a specific way so that it correctly orients inside a particular cartridge-processing system, including if need be to align with illumination and biological sample removal mechanisms. The biological sample could be oriented facing up or down, on flexible, semi-flexible, or rigid portions of the cartridge device. The cartridge device could have just a minimal number of layers, or it could be advantageous to include more layers to ease, improve, or speed-up removal and subsequent processing of targets from the biological sample.

Referring now to FIG. 2A, one preferred embodiment of the invention is shown in which a cartridge device (10) is designed so that it will fully enclose a microscope slide (8) upon which a biological sample (9) has been mounted. As shown in the figure, the cartridge is designed so that the microscope slide will fit into the bottom half (14) of the cartridge device. The size of the cartridges used may vary to suit the sizes of slide available. As shown, the top half (13) of each cartridge contains a film (11) which is connected to a pull tab (12) which extends from one end of the cartridge sufficiently far to allow a user to grip the pull tab effectively. The means by which the top half and bottom half of the cartridge interact may be varied according to means commonly known in the art. The actual mechanism of attaching the top half of the cartridge to the bottom half of the cartridge is not limiting on the invention. For example, the cartridge may be hinged at on end so that the top half of the cartridge may be snapped upward from its position over the slide, or the cartridge may be designed so that the top half of the slide may be detached entirely from the bottom half of the slide. The slide is contained securely within the bottom half of the cartridge regardless of the manner in which the top half of the cartridge interacts with the bottom half of the cartridge. The film is attached to the top half of the cartridge via means commonly known in the art.

FIG. 2B shows the cartridge and slide attached together in accordance with one preferred embodiment of the invention. In this preferred embodiment, the slide (15) is contained completely within the cartridge (16) so that it is inaccessible from the surrounding environment. The cartridge and slide pressing together combines the biological sample (17) on the slide with the film on the cartridge, which is an optical, electro-magnetic or heat-activated substrate or contains specific molecules that allow desired target regions of the biological sample to be extracted. The film can be laid onto the sample after the slide is inserted into the bottom half of the cartridge by, for example, mechanically, electrically, or optically triggering a mechanism within the cartridge that presses the film up against the tissue. Pressing can be accomplished by mechanical, hydraulic, or electrical means or preferably by the imposition of a vacuum. Alternatively, after the slide is inserted, a user can press on the cartridge or can activate a button or switch, or the cartridge may be self-activated, to initiate contact between the substrate and the tissue.

Figure 2C:
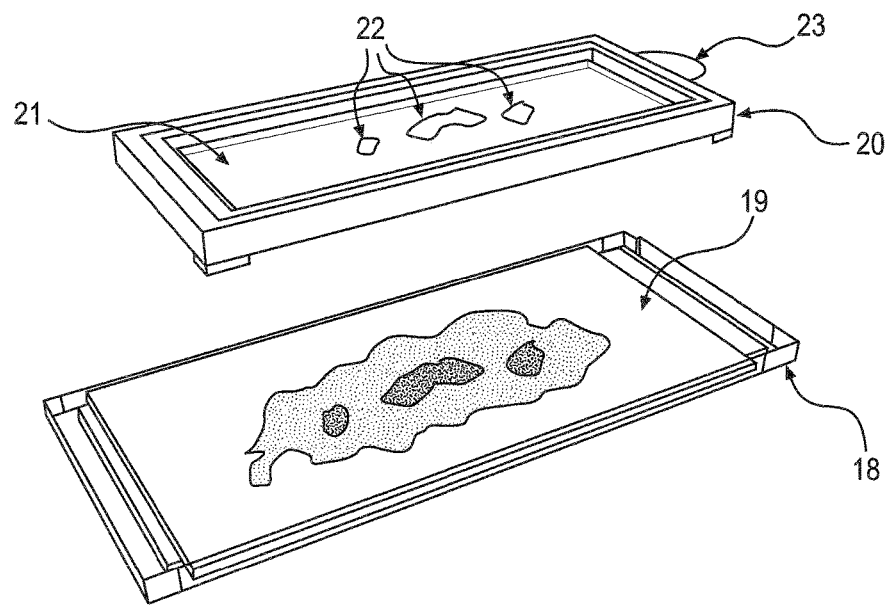
FIG. 2C shows the cartridge opened up after extraction of biological material from the sample on the slide has occurred.

FIG. 2C shows the bottom half of the cartridge (18) and slide (19) after the extraction has been completed and the top half (20) of the cartridge has been raised or detached from the bottom half of the cartridge so that the film (21) may be removed in accordance with one preferred embodiment of the invention. After a suitable period of time, which may be determined by one of ordinary skill according to the particular kind of extraction being performed, the top half of the cartridge is raised from the slide, at which point biological material (22) will also be attached to the film according to the particular extraction technique used. The pull tab (23) is then pulled on by the user to remove the film from the top half of the cartridge.

Figure 2D:
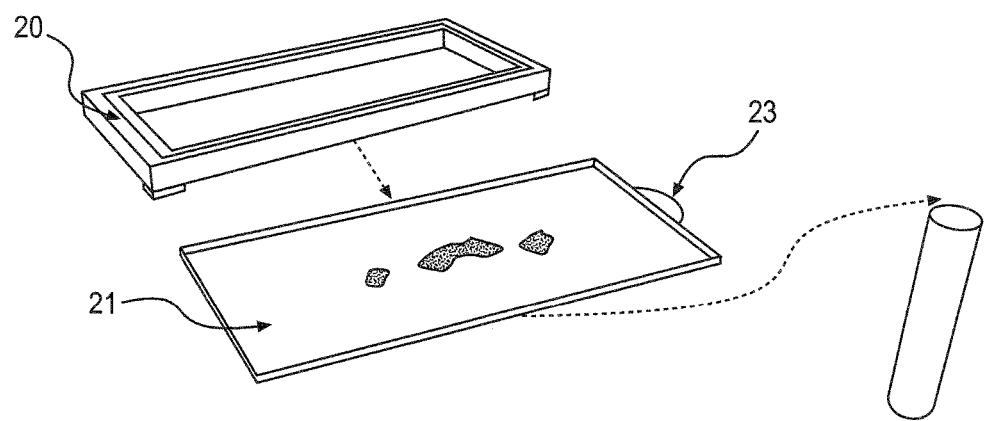
FIG. 2D shows the film on which extracted biological material is adhered removed from the top half of the cartridge.

The film may be imaged while pressed on top of the slide or after the film itself is removed from the cartridge by the pull tab. FIG. 2D illustrates the film (21) removed from the top half (20) of the cartridge by means of the pull tab (23). The film may then be placed in a test tube, vial or other suitable receptacle as shown. After the film has been removed from the top half of the cartridge the film may be further analyzed according to the experimental goals of the user, while the cartridge itself may be re-used or disposed. Cartridges in this preferred embodiment may be made of re-usable plastic or alternative similar materials, which are both inexpensive but durable. The material from which the cartridge is made is not limiting upon the invention.

Cartridge Processing Systems

Figure 3A:
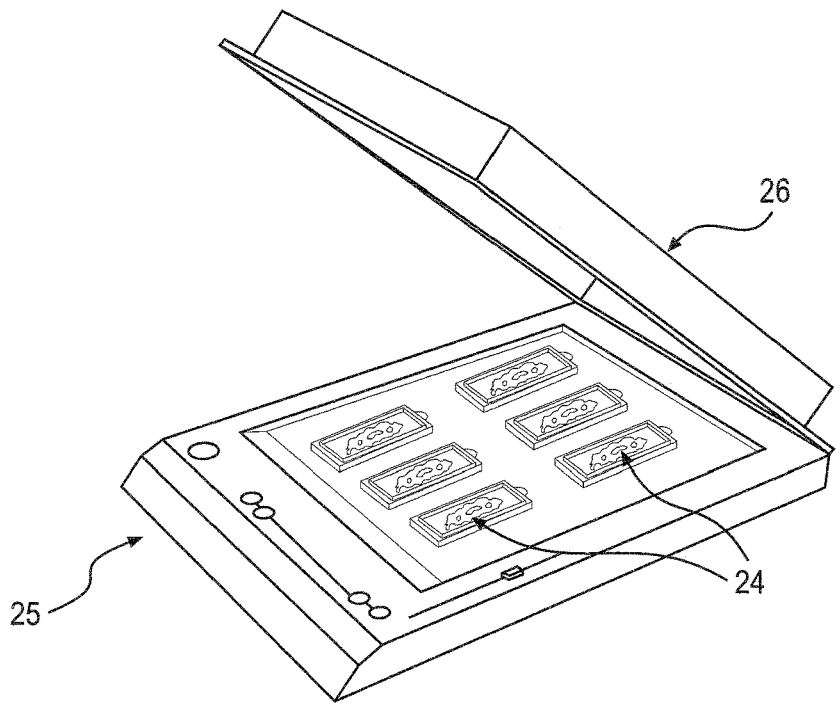
FIG. 3A is a view of a preferred embodiment of the invention, which is a manually operated table-top cartridge processing system designed to enable a user to operate a vacuum seal over cartridges when the lid of the cartridge processing platform is closed.

The cartridge processing system can function "in parallel" or "in series" so that one or many slides with patient tissue may be deposited into one parent device. Referring now to FIG. 3A, one preferred embodiment is shown in which cartridges are processed by an "in parallel" cartridge processing system which is designed to be operated manually. Such "in parallel" cartridge processing systems may be designed as table-top platforms that may be square, rectangular or any other suitable shape. As shown, the system is designed to allow the placement of manually assembled cartridges (24) containing biological samples into a "waffle iron-style" table-top platform (25) designed for that purpose. The platform is then equipped with a hinged lid (26) which is sealed over the cartridges and a vacuum is applied to seal the cartridges by standard means known in the art. The cartridge processing system may be equipped with a timer to control the period for which a vacuum is applied. The user may be alerted to the completion of the vacuum sealing process either through a light or sound emitted by the platform. The hinged lid may then be opened by the user and the cartridges manually extracted and the film removed for further processing/analysis as desired by the user. The hinged lid may be designed to contain, for example, a light or heat source, which can be used to activate adhesion of biological material for extraction to the film contained in each of the cartridges.

In such embodiments, one or many slides with patient tissue could be deposited into a "waffle iron-style" table-top platform, for example, by being laid tissue up or tissue down into receptacles arranged in a preferentially planar configuration in the cartridge-processing system. The slides could be deposited manually, or automatically by a slots and guides, by rollers, by motors, by other mechanical means, by pneumatic means, or by robotic placement. The invention is not limited by the particular manner in which cartridges are placed in the cartridge processing system, or whether the process is manual or automated.

Figure 3B:
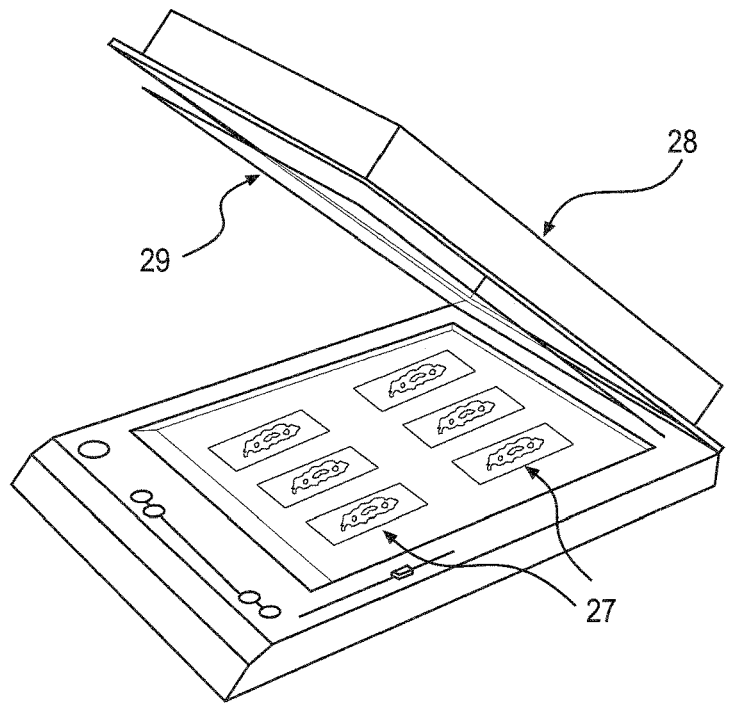
FIG. 3B shows an alternative embodiment of the invention, in which slides with biological samples mounted on them are placed in parallel on a table-top platform designed to bring a substrate into contact with the samples when the lid is closed.

FIG. 3B shows an alternative embodiment of the "in parallel" cartridge processing system, wherein when the lid (28) of the cartridge-processing system is closed over on top of the slides (27) with tissue, a substrate film (29) that is big enough to cover all the slides will be brought into contact with the tissue of the slides. The contact can be improved by pneumatic means (e.g., by air suction) or by mechanical means (pads that press the substrate down onto the tissue of the slides) when the lid is closed. It is understood that the means of ensuring adequate contact between the substrate and the biological tissue for all the samples can be designed per slide or cartridge (e.g., many individual presses, one each above each tissue sample or cartridge) or can be configured to act on all slides or cartridges at once (e.g., one large press that is big enough to cover all slides or cartridges in the planar cartridge-processing instrument). It is also understood that whether slides or cartridges are processed is not limiting on the invention and that all devices disclosed herein may be designed to work with slides or cartridges.

The substrate may also be in the form of, or be part of, a bag. The bottom of the bag may be adhered to the bottom of, for example, a slide-processing instrument while the top of the bag is adhered to the lid of the slide-processing instrument. When the lid is open, the bag is also open, so that the slides or cartridges may be positioned inside the slide-processing instrument, by manual or automated or robotic means. Once the instrument is closed, the bag will be sealed and then can be vacuumed out (air removed) or pressed on by mechanical means to ensure adequate contact between the substrate and all the slides or open cartridges.

In another embodiment, the cartridge-processing instrument can be configured so that there are many substrate bags, including one bag per slide or cartridge or one bag per few slides or cartridges. It is understood that the bag does not have to be made wholly out of substrate material, but only the part of the bag that will come in contact with tissue or biological samples should be made out of the substrate that can bind to tissue regions or molecules of interest.

It is understood that the "in-parallel" cartridge-processing instrument above can be configured in many different configurations, for example the cartridges or slides or other biological samples may be placed horizontally or vertically or at angle, the substrate may be above or below the slides or cartridges, and there are other modifications that will be obvious to someone knowledgeable in the art. This instrument will "in parallel" carry out the steps of laying the substrate up against the tissue on the slide or in or on a cartridge. The substrate would be altered by interaction with the biological sample and then activated by, for example, illumination so that the target region of interest adheres to the substrate. After activation, the substrate would be pulled off with extracted/desired tissue, cells, and molecules on the substrate (for example by opening the lid of the instrument and peeling back the substrate from the tissue or biological samples). After extraction, the substrate could be deposited into receptacles, each single receptacle associated with a single slide or cartridge and then processed (extracted materials released, or substrate dissolved) to deposit the desired selected and purified materials from the patient samples into individual receptacles, for subsequent analysis either in the "in parallel" cartridge-processing instrument or in a subsequent instrument. If in a subsequent instrument (e.g. a DNA screening instrument), the transfer of purified materials from the slide or cartridge-processing instrument could be achieved by mechanical or pneumatic or robotic means. In particular, the cartridge-processing and subsequent instrument could have matching interfaces (same location of slots for samples) so that transfer of materials from one to the other would be simple, reliable, fast, and convenient.

Figure 4:
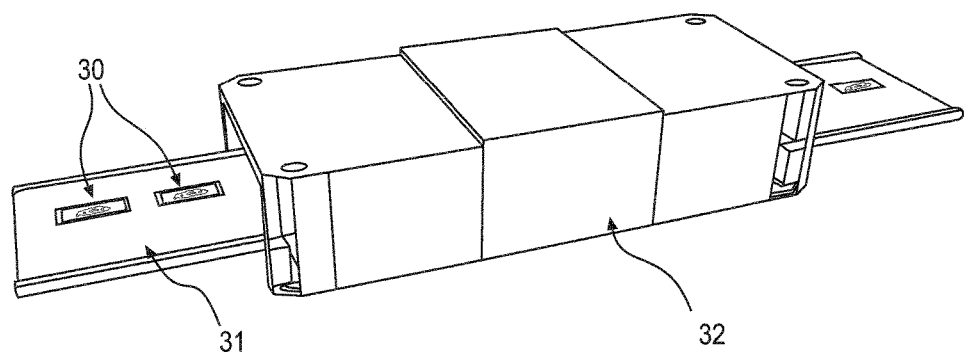
FIG. 4 is a view of a preferred embodiment of the invention, which is an "in series" cartridge processing system, which is designed to operate semi-automatically.

Referring now to FIG. 4, one preferred embodiment is shown in which cartridges are processed by an "in series" cartridge processing system, which is designed to operate semi-automatically. Cartridges containing biological samples (30) may be manually assembled and then placed on a platform (such as a conveyor belt (31)) designed to convey cartridges in series into a vacuum sealing device (32). After the vacuum sealing process has been applied, the cartridge processing system is then designed to convey the cartridge out of the vacuum sealing device, after which the film may be extracted for further processing/analysis as desired by the user. The invention is not limited by the design of the "in series" conveyance system, the method of sealing the film or whether the device is primarily manually operated or automatically operated.

Figure 5:
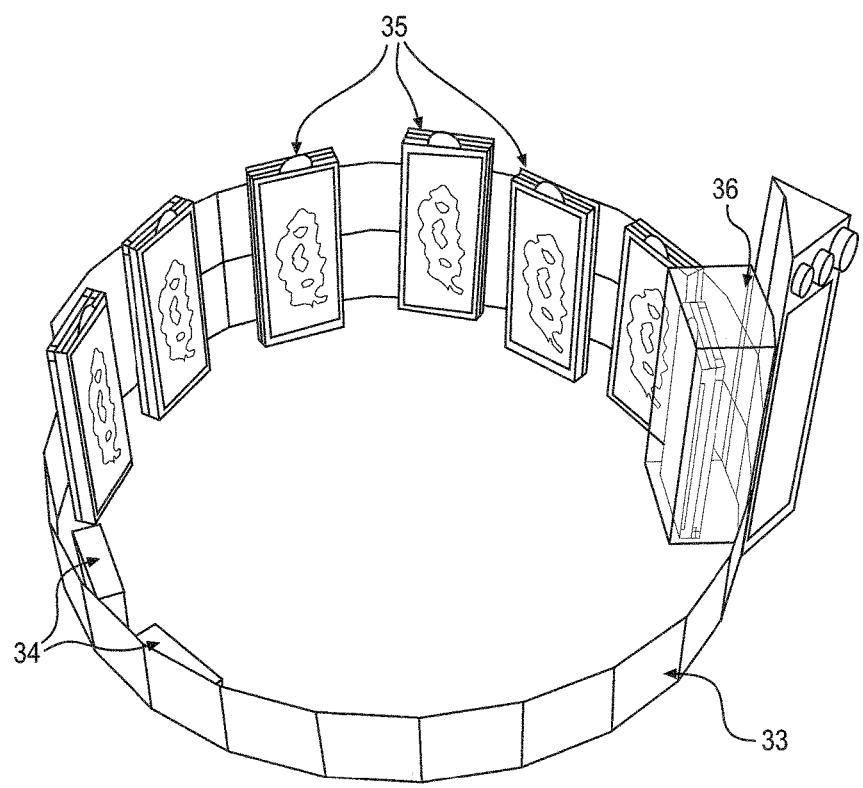
FIG. 5 is a view of a preferred embodiment of the invention, which is a cartridge-processing system may be designed as a carousel where cartridges with tissue are entered into slots, and rotation of the carousel causes each cartridge to be processed.

Referring now to FIG. 5, in one preferred embodiment of the invention a cartridge-processing system may be designed as a carousel (33) where slides or cartridges (35) with tissue are entered into slots (34), and rotation of the carousel causes each cartridge to be processed. Cartridges containing biological samples may be manually assembled and then placed on a carousel designed to convey cartridges in series into a vacuum sealing device (36) or to a device with a different sealing mechanism (e.g. mechanical pressing force to seal triggered by mechanisms within or outside the cartridge/slide). After the vacuum sealing process has been applied, the cartridge processing system is then designed to convey the cartridge out of the sealing device, after which the film may be extracted for further processing/analysis as desired by the user. The invention is not limited by the design of the carousel, the method of sealing the film or whether the device is primarily manually operated or automatically operated.

In some embodiments, the slides or cartridge can be inserted into a cartridge-processing system that illuminates and images the cartridge. Such a cartridge processing system may be designed to efficiently and automatically process one or more cartridges while recording such images.

Figure 6:
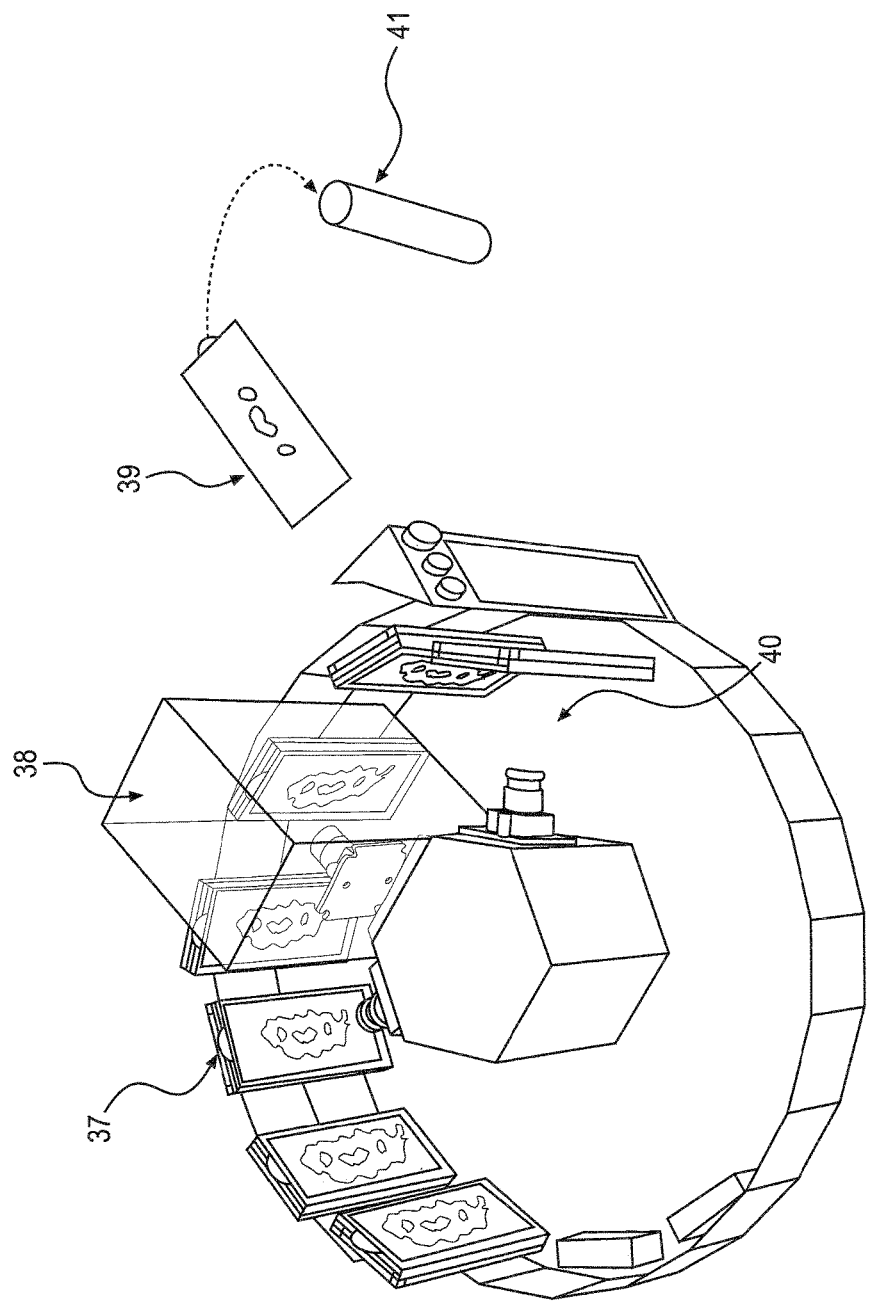
FIG. 6 is a view of a preferred embodiment of the invention, which is a cartridge assembly system to creates and processes the cartridge devices through an automated process.

Referring now to FIG. 6, in another embodiment of the invention the slides or cartridge can be inserted into a parent cartridge-processing system that illuminates and images the cartridge, and the cartridge design allows the extraction of desired regions of the biological sample in a fast and efficient manner, including in a single step. Such a parent instrument will efficiently and automatically process one or more cartridges. It will ensure that the substrate contacts the tissue or biological samples, will activate the substrate to selectively bind to specific tissue regions, cells, and molecules of interest (e.g. cancer cells from a milieu of many other cells), and will then extract those tissue regions, cells, and molecules of interest. The parent cartridge-processing system could be designed as a carousel where slides with tissue are entered into slots, and rotation of the carousel causes each slide to be processed.

For instance, in a first location (37) the substrate could be laid up against the tissue on the slide and imaged; in a second location (38) the substrate could be activated; in a third location (39) the substrate could be pulled off with extracted/desired tissue, cells, and molecules on the substrate; in a fourth location (40) the slide could be reimaged; and in a fifth location (41) the substrate could be deposited in a receptacle and processed (extracted materials released, or substrate dissolved) to deposit the desired selected and purified materials from the patient samples into the receptacle. Slides with tissue samples, or other bio samples, would be moved from one location to the next, thus ensuring that many patient slides are processed in sequence by the carousel cartridge-processing system. The extracted and purified materials for each sample could then be analyzed (DNA screens, protein analysis, drug or therapy screens or binding analysis) in the parent cartridge-processing system, or could be manually or automatically provided by a downstream instrument or system.

The transfer of purified materials from the slide or cartridge-processing instrument to another subsequent analytical instrument can be achieved by mechanical or pneumatic or robotic means. In particular, the cartridge-processing and any subsequent instrument may have matching interfaces (same location of slots for samples) so that transfer of materials from one to the other would be simple, reliable, fast, and convenient.

Cartridge Assembly Systems

We also disclose a cartridge assembly system to create the cartridge devices. This assembly system could be part of the cartridge-processing system that will process the cartridge device, or it could be a separate system. In the cartridge assembly system, biological samples, such as tissue sections, whole tissue samples, histology slide, biopsy material or samples, frozen or fixed (e.g., formalin, paraffin, or ethanol fixed) samples, cellular specimens or cellular preparation, cell smears, cytology preparations, and biofilms are attached to the cartridge backing by stamping, rolling, or other types of applied pressure, by shrink sealing, or by other mechanical or chemical means. The assembly system takes in the biological sample, orients it to the cartridge backing or orients the cartridge backing to the biological sample, and then creates and seals the cartridge by the above mentioned means.

The cartridge could also be combined with necessary reagents provided in a kit supplied to the user. For example, the cartridge assembly system could take in a biological sample, cartridge materials (e.g., backings, films, etc), and any necessary reagents provided in the kit (e.g., optical, electro-magnetic, or heat activated molecules, chemicals, biomolecules, liquid or solid reagents, ligands, antibodies, fusion molecules, polymers, visualizing agents, proteins, DNA, mRNA, enzymes, lipids, carbohydrates, etc), and process them to make the assembled cartridge device. Together, the cartridge materials and the reagents in the kit would provide all the necessary materials to carry out extraction of the desired region, regions, or molecules from the biological samples.

Post-Cartridge Processing Analysis

Slides or cartridges are processed by either an "in-series" or "in-parallel" cartridge-processing instrument, which will extract and purify genes (DNA, mRNA, etc), proteins, cancer cells, or other materials/molecules from patient samples on a per sample basis. After this process, to integrate tissue, cell, and molecule extraction and purification with genetic and protein screens, the purified materials will be screened for nucleotides or proteins using methods known in the art.

For instance, after processing in the cartridge-processing instrument, purified samples would be deposited automatically or robotically into vials or test tubes, with purified materials from each sample being deposited into a separate vial or test tube. In a carousel "in-series" configuration, vials or test tubes could be underneath the carousel and once each sample has been extracted and purified, it would be deposited into a vial or test tube.

Similarly, in an "in-parallel" slide or cartridge processing instrument, slides or vials or other receptacles would, for example, be placed underneath each slide or cartridge, and purified materials would be deposited into them. In a preferred embodiment, purified material from each slide or cartridge would be deposited into one vial or receptacle. The genetic material would then be analyzed, e.g., screened for the presence or absence of one or many specific genes or gene fragments or DNA or mRNA sequences, using currently known methods or future methods. Likewise, protein or other material could also be screened, quantified, or analyzed using known methods or future methods. Such analysis could be done within the same instrument, or could be done in a downstream instrument. If in a downstream instrument, we disclose design of the interface between the two instruments for reliable, fast, and convenient transfer of materials. For example, instruments can be designed to operate with two layers, one layer which performs the extraction and another layer that performs the analytical stages.

For example, DNA analysis could occur in an instrument placed underneath the slide or cartridge-analysis instrument, where the vials or test tubes (each filled with purified material from a single sample) would drop down or be mechanically or pneumatically or electrically lowered into the DNA screening instrument. The two instruments would have the same spatial arrangement of slides/cartridges and vials/test tubes (or other receptacles) so that transfer of materials from one to the other would be convenient, error free, simple, and fast. It is understood that other embodiments are possible, for example transfer of materials could be horizontal instead of vertical, up instead of down, at an angle, could be achieved robotically or by other means.

The invention also discloses methods for integrating biological sample purification with screening and selection of drugs or therapies for patients. As above, purified materials (e.g., tissue, cells, nucleotides, proteins, or other biological matter) would be provided to another part of the same instrument or to a subsequent instrument. Drugs or therapy would then be screened against purified materials more effectively than against unpurified materials, using known methods. For example, in each vial, test tube, or other receptacle (one receptacle per patient sample in a preferred embodiment), known or future drug selection screens could be carried out. Drug or therapy binding or activity to purified materials could be tested per receptacle.

It also may be advantageous to provide purified patient materials to live cell cultures, to test expression of nucleotides in live cells, or to carry out drug and therapy screens against living cells that have been combined with purified materials from each patient sample.

For example, cancer genes from patients may be incorporated into living cells, expressed, and then tested against drugs or other therapies. It may be advantageous to have different materials from a single patient samples deposited into multiple receptacles and live cell cultures (e.g., patient cancer genes into one vial with cells, patient immune cells into a second vial, to test if drugs can modulate a patient's immune response to better kill cells that are expressing that patient's cancer genes). Thus the invention also discloses instruments that will deposit materials from one sample into multiple different receptacles. For example, in an instrument designed with two layers, one layer for extraction and another layer for analysis, the analytical layer for each slide/cartridge may provide up to three or more different vials for depositing of the extracted biological materials for further analysis.

Conversely, the invention also discloses deposition of materials from multiple samples into one receptacle, e.g., for further material enrichment (e.g., DNA from cancer cells from 5 slides from the same patient all deposited into one vial, to provide more DNA for that patient). Computer programs and software can track which samples are where. Radio-frequency (RF) tags, colored markings, mechanical tabs, or other known or future means may also be used to mark and keep track of cartridges, vials and test tubes to provide an extra layer of tracking to know which samples are where.

Layered Imaging

In cancer, and in other diseases, a big part of patient diagnosis is observation of the shape and colors of tissues and cells (tissue/cell morphology). The invention discloses improved morphology analysis by providing pre-extraction and post-extraction images for tissue samples, as well as overlaying nucleotide and protein and other molecular information on tissue images. In the disclosed slide and cartridge-processing instruments, a high-resolution camera or cameras and software will be provided. The camera or cameras will take high-resolution photographs of all samples at each stage. The first image could be similar to morphology (histology) images already used routinely in the clinic and in pathology labs (e.g., H&E stains or other stains or unstained). Once of-interest tissue is removed (e.g., cancer cells, or other diseases cells), photographs or images will be taken of removed and remaining tissue.

Location of removed tissue (e.g., location of the cancer) could then be accurately displayed to the clinician or pathologist overlaid on top of the original image for each patient's sample. This would provide the clinician/pathologist with additional information (e.g., exactly where the cancer is and what areas of the slide were sampled) and would aid diagnosis and subsequent selection of treatment. Further, image analysis could provide an estimation of the amount of biological material removed from the sample, and this information may allow for better decisions on the amount and/or type of downstream testing (e.g. if a large amount of tissue is sampled the software may determine that there is enough cellular material for numerous downstream tests versus when only a small amount of tissue is sampled providing only for a single test).

When additional information is collected, e.g., which cancer genes are present in that patient's cancer cells, that information could also be overlaid on top of the image, in a useful way (as transparent colors, as animated layers, as a 3-dimensional layered image, as a clickable image, or by other known or future means that will provide effective information visually). That will further improve diagnosis and treatment capabilities. Now the clinician or pathologist will be able to see which genes are present where, for example, and better diagnose and select treatment.

For example, this will allow better estimation of the extent of tumors in patients. Protein, antibody, and other information could also be overlaid on the images. Further additional information, e.g., when genes in this region where expressed in cells, this drug was able to treat those cells, could also be overlaid. The practitioner would be provided with a rich set of information useful for diagnosis and treating patients—for example, they could see which drugs will be useful for which regions of the tumor, thus selecting the combination of drugs that can treat the whole tumor or focusing drugs on the invasive elements of the patient's tumor.

A person knowledgeable in the art would recognize that there are many other embodiments, various genetic screens, various drug screens, various visual presentations, that are equivalent to the ones presented here. Integrating patient sample purification with genetic, protein, and drug analyses, and presenting that data to clinicians and pathologists, could dramatically improve patient diagnosis and treatment.

The invention further discloses automated image processing to suggest diagnoses and treatments. The shapes and colorings of cells that are associated with diseases are known to a degree. Genetic and protein profiles that are associated with disease are also beginning to become known, and will be known better in the future.

The invention discloses instruments that store, retrieve and couple images of tissue samples, as described above, with databases for morphology, genetic screens, protein screens, and other bio-molecules correlated to disease databases, and discloses software that will suggest diagnosis and treatment options to physicians.

For example, if an image of a patient's tissue samples shows a shape that is potentially correlated with cancer but the shape and coloring of the cells is not sufficient to make a diagnosis of cancer, we disclose adding additional metrics, such as: 1) percent cells with expressed antibody that is indicative of cancer and that would bind to our substrate and be made visible; and 2) genes that are correlated with that type of cancer. Presenting a clinician with morphology plus antibody plus gene evidence of cancer, automatically, would suggest a much higher likelihood of cancer and would enable software to suggest a diagnosis of cancer. Likewise, layering together information from morphology, genes, and live cell responses, for example, could also suggest therapy. If the clinician can see that invasive portions of the tumor have genes of a certain type and when those genes were expressed in cells responded well to a certain drug, that would indicate that this drug could be a viable treatment option for that patient.

Data Handling, Patient Records

The invention discloses tags (e.g., color, RF tags, mechanical tags, electrical tags, others) and software and hardware for automated sample and data management. In one embodiment, each slide or cartridge would be marked with a sample or patient specific identifier. From then on, in every step of the process, the location, status, and processing of the sample would be tracked by tags and software. Readers in the instrument and software will assign images (e.g., morphology photographs) to each sample, before and after tissue extraction. Images of extracted and left-behind tissue will be taken and associated with before images. When the purified materials are deposited into a vial, test tube or receptacle, that receptacle will be tracked in software and hardware.

Subsequent analysis (genetic screening, protein screening, drug or therapy screens, live cell culture screens) will also be tracked, again by tags on receptacles and by software, to keep track of which screens apply to which original samples. When information from gene and drug screens is overlaid back onto the original images of tissue samples, that too will be tracked by software and stored in a database. The clinician or pathologist will be able to query any part of the process—they will be able to pull up and examine any image or data at any stage.

Furthermore, in a preferred embodiment, collected data will be automatically transmitted to patient records. When a clinician reviews a patient's record, rich layered data for that patient's samples will be available. Clinicians will be able to access such data remotely from the stored database, either after or during patient sample processing. In an another embodiment, a clinician or pathologist will be able to remotely manipulate the instruments that carry out the sample purification and collect the images and data.

The invention further discloses methods to follow patients as they progress through disease and treatment. When a patient returns for a follow up visit, his or her samples will be identified with a patient identifier that is linked to that same patient. Analysis of patient samples will proceed as above, but in addition the data and images for the follow up visit will be linked with data and images from the previous visit. Original and follow-up images and data will be presented to the clinician or pathologist side-by-side, or overlaid one on top of the other, or as an animation, or by other known or future means, so that the practitioner can readily see the progression of the patient, and can assess if treatment is or is not working effectively. That will enable clinicians to better track patient outcomes and the efficacy of therapy, and will enable better selection of treatment for patients.

Practitioners will be able to access data and images remotely. Integration of software and substrates, slides, cartridges, and cartridge-processing instruments hardware with pathology laboratory workflow and with existing and emerging genetic, protein, and drug screens, will enable superior analysis, diagnosis, follow up, and treatment of patients. Software integrated with these systems will provide an improved service to clinicians and pathologists, and will enable improved patient care.

While enabling practitioners to obtain superior analysis, diagnosis, follow up, and treatment of patients, patients will also benefit by our systems. Additional software and communication tools between the practitioner and patient will also be developed to not only include information placed into electronic medical records but also to provide patients with health related information such as treatment follow-up, treatment choices and disease management protocols.

The invention further discloses linking collected data and images to existing disease and pathology databases. In one embodiment, collected morphology images and overlaid genetic markers for cancer will be cross-referenced with existing databases of cell morphology (e.g., cancer progression scoring tests) and genetic markers for cancer. Searching algorithms will provide a clinician or pathologist with links to relevant hits (similar cell morphology, shared genetic markers) in cancer databases. Thus, when a clinician or pathologist views that patients record, our disclosed systems will not only provide tissue sample morphology overlaid with genetic information and potential drug response metrics, it will also score that morphology and genetic profile against known cancer databases.

Additional Indications/Overall Use

In the above, illustrative examples have been largely provided for cancer. However, one knowledgeable in the art would recognize that the same methods are useful for other diseases and pathologies besides cancer. We disclose using the methods described above for other diseases or pathologies, including diseases or pathologies with a genetic predisposition or component.

The disclosed integrated hardware and software system will start with a patient's sample, and will, in one automated overall system, progress that sample all the way from initial mounting through purification to genetic and drug screening. It will provide the practitioner with an integrated and automated work flow, all in one lab with one set of instruments, to go from initial patient sample to final disease diagnosis and therapy screening. The results will be automatically tied to patient records, will be accessible remotely and in real time, and will allow monitoring of patient response to therapy through subsequent follow up visits.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present invention.

What is claimed is:

1. A cartridge for extracting biological material from a biological sample, the cartridge comprising:

a film pre-loaded on the cartridge, wherein the film comprises a substrate suitable for extracting biological material from the biological sample;

an adjustable link for attaching the cartridge to a slide upon which the biological sample has been mounted, wherein the cartridge and slide form a single unit after attaching the cartridge to the slide;

a pull tab which is attached to the film, wherein the pull tab enables the film to be removed from the cartridge.

2. The cartridge of claim 1, wherein the adjustable link for attaching the cartridge to the slide upon which the biological sample has been mounted, comprises hooks or grooves that enable attachment of the cartridge to the corners of the slide.

3. The cartridge of claim 1, wherein the adjustable link for attaching the cartridge to the slide upon which the biological sample has been mounted, comprises a groove which enables the entire slide to be fully enclosed by the cartridge when the film is pressing against the biological sample mounted on the slide.

4. The cartridge of claim 1, wherein the adjustable link for attaching the cartridge to the slide upon which the biological sample has been mounted, comprises a groove which enables the slide to be attached to the cartridge by three or fewer sides of the slide.

5. The cartridge of claim 1, wherein the cartridge enables the film to be imaged while the film is pressed against the biological sample mounted on the slide, or imaged after the film is pressed against the biological sample mounted on the slide.

6. The cartridge of claim 1, wherein the cartridge is disposable after being used to extract biological material from a biological sample.

7. The cartridge of claim 1, wherein the cartridge is re-usable after being used to extract biological material from a biological sample.

8. The cartridge of claim 1, wherein a material forming the film comprises polymer, polystyrene, wax, rubber, silicon, silicone, paper, cloth, metal, alloys, an impregnated web, or a liquid material that dries or otherwise hardens to form a flexible, semi-flexible, or rigid covering.

9. The cartridge of claim 1, wherein a material forming the cartridge comprises glass, silicon, polymer, polystyrene, plastic, rubber, paper, wood, metal, or alloys.

10. The cartridge of claim 1, wherein the cartridge comprises rigid, semi-rigid or flexible layers.

11. The cartridge of claim 1, wherein the film is readily dissolvable.

12. The cartridge of claim 1, wherein the film is a substrate which enables biological material attached to the substrate to be readily removed from the substrate.

* * * * *